_US005597567A_

United States Patent [19]

Whitcup et al.

[11] Patent Number: 5,597,567
[45] Date of Patent: Jan. 28, 1997

[54] BLOCKING CELL ADHESION MOLECULES AND TREATING ANIMALS WITH OCULAR INFLAMMATION

[75] Inventors: Scott M. Whitcup, Rockville; Chi-Chao Chan, Kensington; Robert B. Nussenblatt, Bethesda, all of Md.

[73] Assignee: The United States of America as represented by the Department of Health and Human Services, Washington, D.C.

[21] Appl. No.: 192,198

[22] Filed: Feb. 4, 1994

Related U.S. Application Data

[63] Continuation of Ser. No. 822,042, Jan. 17, 1992, abandoned, which is a continuation-in-part of Ser. No. 770,026, Oct. 4, 1991, abandoned.

[51] Int. Cl.$^6$ ............................ A61K 39/00; C07K 16/28
[52] U.S. Cl. ............................. 424/143.1; 530/388.72; 530/388.85; 530/389.1
[58] Field of Search ................... 424/143.1; 530/388.22, 530/388.85, 389.1

[56] References Cited

FOREIGN PATENT DOCUMENTS 0289949  9/1988  European Pat. Off. ........ C12N 15/00

OTHER PUBLICATIONS

Zimmerman et al Arch Ophthalmol 102:551–553 1984.
Zimmerman et al Am J Ophthalmology 114:8–13 1992.
Schen et al Arvo Meeting Abstract 3888–2 1993.
Junghans et al Cancer Research 50:1495–1502 1990.
Harris et al TibTech 11:42–46 1993.
Waldmann Science 252:1657–1662 1991.
Liversidge, et al Immunology 1990, 71:390–396.
Osband et al., Immunotherapy 11(6):193–195 (1990).
Dillman, Ann. Internal Med. 111:592–600 (1989).
Hird et al, Genes and Cancer (1990) chapter 17.
Cunningham et al., TIBTECH 10(1992).
Kettleborough et al., Protein Engineering 4(7):773–783 (1991).
Emery et al., Exp. Opin. Invest. Drugs 3(3):241–251 (1994).
Kozak et al., Eur. J. Immunol. 17:541–547 (1987).
Dua et al., Clin. Exp. Immunol. 75:100–105 (1989).
Forrester, J. R. et al. Curr Eye Res 9:183–191 Supp. 1990.
Bevilacqua et al. Science 243:1160–1165.
Takei, Fumio J. Immunol. 134:1403–1407, 1985.
Hutchings et al. Nature 348:639–642, 1990.
Lynn et al. J. Immunol. 147:3072–3079, 1991.
Picker et al. Nature 349:796–799, 1991.
Elner et al. Amer. J. Pathol. 138:525–536, 1991.
Cosimi et al. J. Immunol. 144:4604–4612, 1990.
Forrester, J. Y. et al. "Regulation of the local immune response by retinal cells" Research (1990) B:183–191 Supp.
Bevilacqua, Michael P. et al. "Endothelial Leukocyte Adhesion Molecule 1: An Inducible Receptor for Neutrophils Related to Complement Regulatory Proteins and Lectins" Science 243:1160–1165.
Takei, Fumio "Inhibition of Mixed Lymphocyte Response by a Rat Monoclonal Antibody to a Novel Murine Lymphocyte Activation Antigen (MALA-2)" The Journal of Immunology (1985) 134:1403–1407.
Hutchings, Patricia et al. "Transfer of diabetes in mice prevented by blockade of adhesion–promoting receptor on macrophages" Nature (1990) 348:639–642.
Lynn, W. A. et al. "Lipopolysaccharide–induced Stimulation of CD11b/CD18 Expression on Neutrophils" The Journal of Immunology (1991) 147:3072–3079.
Picker, Louis J. et al. "ELAM–1 is an adhesion molecule for skin–homing T cells" Nature (1991) 349:796–799.
Elner, Victor M. et al. "Intercellular Adhesion Molecule–1 in Human Corneal Endothelium" American Journal of Pathology (1991) 138:525–536.
Cosimi, A. Benedict et al. "In Vivo Effects of Monoclonal Antibody to ICAM–1 (CD–54) In Nonhuman Primates With Renal Allografts" The Journal of Immunology (1990) 144:4504–4512.

Primary Examiner—Donald E. Adams
Attorney, Agent, or Firm—Needle & Rosenberg, PC

[57] ABSTRACT

The present invention relates, in general, to a method of blocking of cell adhesion molecules. In particular, the present invention relates to a method of blocking cell adhesion molecules with monoclonal antibodies or synthesized substances.

12 Claims, 12 Drawing Sheets

BLOCKING CELL ADHESION MOLECULES AND TREATING ANIMALS WITH OCULAR INFLAMMATION

This application is a continuation of application Ser. No. 07/822,042, filed Jan. 17, 1992, now abandoned which application is a continuation in part of application Ser. No. 07/770,026, filed Oct. 4, 1991 now abandoned.

BACKGROUND OF THE INVENTION

1. Field of the Invention

The present invention relates, in general, to a method of blocking cell adhesion molecules. In particular, the present invention relates to a method of blocking cell adhesion molecules with monoclonal antibodies or synthesized substances.

2. Background Information

Cell adhesion molecules are surface proteins that mediate cell binding, and the expression of these molecules can promote the migration of leukocytes to areas of inflammation. One of these cell adhesion molecules, intercellular adhesion molecule-1 (ICAM-1), can be expressed on the human cornea and retinal pigment epithelium (RPE)(Elner, V. M. et al., Am. J. Path. (1991) 138:525–536; Kaminska, G. M. et al., Invest. Ophthalmol. Vis. Sci. (1991) 32 (Supp):677; Forrester, J. V. et al., Curr. Eye Res. (1990) 9 (Supp):183-191). Lymphocyte function-associated antigen-1 (LFA-1), a member of the integrin family of cell adhesion molecules, is the counter receptor for ICAM-1. In contrast to ICAM-1 which can be expressed on several ocular tissues, LFA-1 is predominantly expressed in leukocytes (Albelda, S. M. et al., FASEB, J. (1990) 4:2868–2880; Springer, T. A., Nature (1990) 346:425–434). The interaction of ICAM-1 and LFA-1 is felt to be important in regulating and guiding the migration of lymphocytes to sites of inflammation. Another adhesion molecule, endothelial leukocyte adhesion molecule-1 (ELAM-1), is expressed on the corneal endothelium in endotoxin induced uveitis (EIU) in the Lewis rat (Whitcup, S. M. et al., Invest. Ophthalmol. Vis. Sci. (1991) 32 (Supp):677).

SUMMARY OF THE INVENTION

The goal of the present invention is to demonstrate that cell adhesion molecules are expressed on tissues in the eye during ocular inflammation and to show that by blocking these cell adhesion molecules, inflammatory eye disease can be inhibited. Studies on human ocular tissue and in two animal models of inflammatory eye disease, 1) endotoxin induced uveitis (EIU) and 2) experimental autoimmune uveitis (EAU), were performed.

Expression of cell adhesion molecules has been demonstrated in other tissues during inflammation, and blockage of these cell adhesion molecules has resulted in inhibition of inflammation. Several cell adhesion molecules have been demonstrated on ocular tissues in vitro and in vivo by other investigators (Elner, V. M. et al. (1991) Am J Path 138:525–536; Kaminska et al. (1991) Invest Ophthalmol Vis Sci 32(Supp) 677; Forrester et al. (1990) Curr Eye Res 9(Supp) 183–91).

It is a general object of this invention to provide a method of treating an animal with ocular inflammation.

It is a general object of this invention to provide a method of blocking a cell adhesion molecule in an animal.

Further objects and advantages of the present invention will be clear from the description that follows.

DETAILED DESCRIPTION OF THE INVENTION

Cell adhesion molecules are expressed on inflammatory cells and on ocular tissue. The binding of cell adhesion molecules expressed on inflammatory cells to their corresponding counter-receptors expressed on ocular tissues fosters the development of inflammation in the eye. By using monoclonal antibodies or synthesized molecules to block these cell adhesion molecules, ocular inflammation can be inhibited.

In one embodiment, the present invention relates to a method of treating an animal with ocular inflammation comprising administering to said animal a therapeutically effective amount of an antibody or synthesized substance having binding affinity for a cell adhesion molecule under conditions such that said treatment is effected.

Suitable pharmaceutically acceptable diluents, carriers, and excipients are well known in the art.

One skilled in the art will appreciate that the amounts to be administered for any particular treatment protocol can readily be determined. Suitable amounts might be expected to fall within the range of 10 μg/dose to 10 g/dose, preferably within 10 mg/dose to 1 g/dose.

These substances may be administered by techniques known in the art (preferably systemically, via periocular injection, or topically to the eye as eye drops or ophthalmic ointment). This local administration can limit potential systemic side effects, but still allow control of ocular inflammation. Current treatment of ocular inflammation centers around the use of steroids with a number of unwanted adverse effects such as glaucoma and cataract, which can be avoided with this new anti-inflammatory therapy for ocular inflammation.

In one preferred embodiment, the ocular inflammation (preferably, iritis or anterior uveitis) results from trauma or disease. The antibody or molecules to block adhesion molecules can be delivered by:

1. topical drops or ointment,
2. periocular injection,
3. systemically by intravenous injection or orally.

Figure 9A:
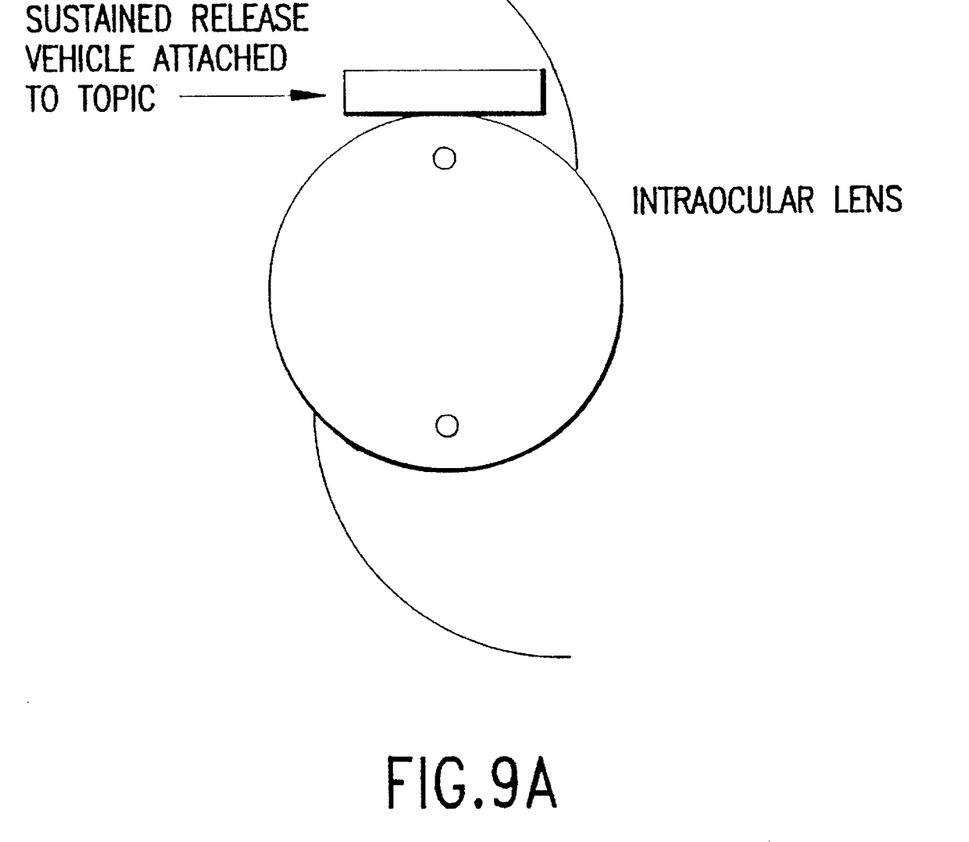
FIG. 9A. Intraocular lens delivery of anti-adhesion molecule drugs using a sustained release vehicle attached to optic.
Figure 9B:
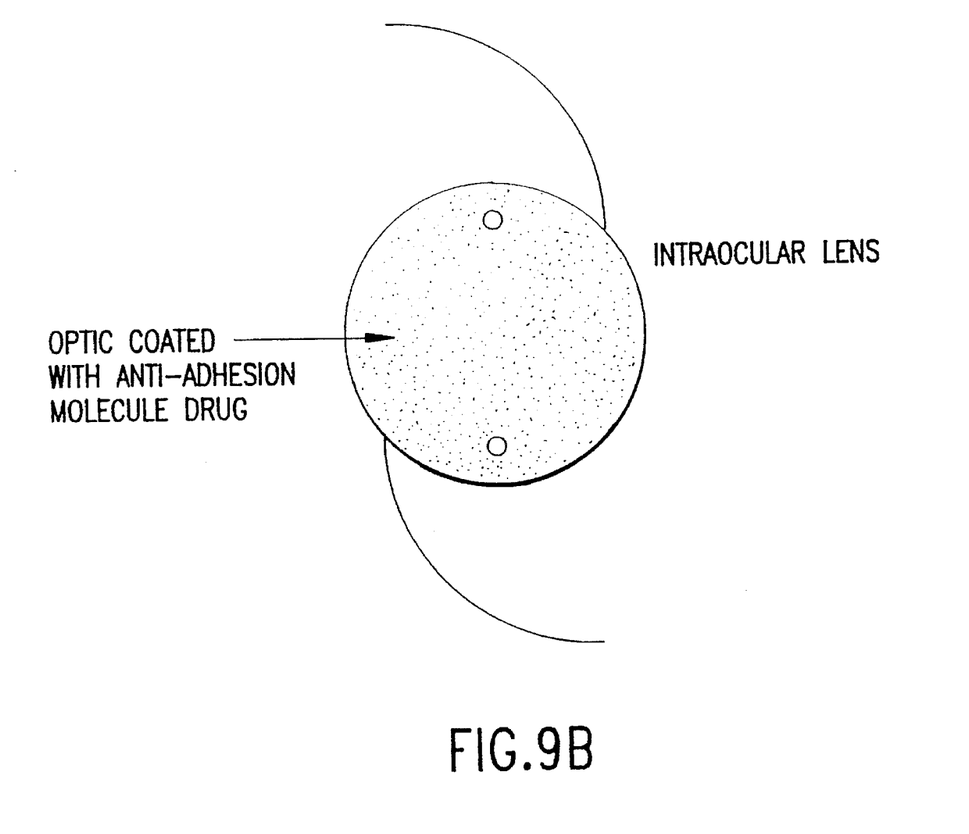
FIG. 9B. Intraocular lens delivery of anti-adhesion molecule drugs using an optic coated with anti-adhesion molecule drug.

In another preferred embodiment, the ocular inflammation is post-surgical inflammation. The antibody or molecules to block cell adhesion molecules can be delivered by:

1. topical drops or ointment,
2. periocular injection,
3. systemically by intravenous injection or orally,
4. intracamerally into the anterior chamber or vitreous,
5. via a depot attached to the intraocular lens implant inserted during surgery (FIG. 9A),
6. via a surface coating of the intraocular lens implant inserted during surgery (FIG. 9B), or
7. via a depot placed in the eye sutured in the anterior chamber or vitreous.

In yet another preferred embodiment, the inflammation results from post-surgical corneal graft rejection. The antibody or molecules to block cell adhesion molecules can be delivered by:

1. topical drops or ointment,
2. periocular injection,
3. systemically by intravenous injection or orally,
4. intracamerally into the anterior chamber or vitreous,
5. via a depot attached to the intraocular lens implant inserted during surgery, or
6. via a depot placed in the eye sutured in the anterior chamber or vitreous.

In a further embodiment, the ocular inflammation is posterior uveitis. The antibody or molecules to block cell adhesion molecules can be delivered by:

1. topical drops or ointment in aphakic patients
2. periocular injection
3. systemically by intravenous injection or orally
4. intracamerally into the anterior chamber or vitreous
5. via a depot attached to the intraocular lens implant inserted during surgery
6. via a depot placed in the eye and sutured in the anterior chamber or vitreous.

In another embodiment, the present invention relates to a method of blocking a cell adhesion molecule in an animal comprising administering to said animal a sufficient amount of an antibody having binding affinity for said cell adhesion molecule such that blocking of said molecule is effected. More specifically, the present invention relates to a method of blocking cell adhesion molecules during ocular inflammation (preferably, the ocular inflammation is as described above). The quantity of antibody used can be determined by one skilled in the art.

The present invention is described in further detail in the following non-limiting Examples.

EXAMPLES

The following protocols and experimental details are referenced in the Examples that follow:

Report of Cases:

Case 1 A 27-year-old black woman with biopsy proven sarcoidosis developed bilateral iritis with iris nodules (Chan, C-C. et al., Arch. Ophthalmol. (1987) 105:1398–1402). Despite systemic and periocular steroid injections, the patient developed progressive anterior and posterior segment inflammation of the left eye with rubeosis iritis. The left eye became blind, painful, and hypotonus, and was enucleated.

Case 2 A 72-year-old black woman with a 30-year history of bilateral recurrent panuveitis with exudative retinal detachments, apapilledema, hearing loss, and vitiligo was diagnosed with Vogt-Koyanagi-Harada syndrome (Chan, C-C. et al., Am. J. Ophthalmol. (1988) 105:607–611). The patient underwent a peripheral iridectomy and subsequent cataract extraction of the right eye for angle closure glaucoma caused by lens subluxation. The right eye was enucleated following the development of painful neovascular glaucoma with loss of vision.

Case 3 A 24-year-old woman developed progressive bilateral loss of vision with white, fibrotic subretinal lesions and mild vitritis (Kim, M. K. et al., Am. J. Ophthalmol. (1987) 104:15–23). The patient failed to respond to systemic steroids and cyclophosphamide. The patient elected to have a diagnostic enucleation of the right eye after her vision deteriorated to hand motions in the right eye and 20/200 in the left eye. A diagnosis of subretinal fibrosis and uveitis syndrome was made based on the histopathologic findings.

Case 4 A 38-year old white man developed bilateral granulomatous uveitis 6 months after a ruptured right globe secondary to blunt trauma (Chan, C-C. et al., Ophthalmology (1986) 93:690–5). The patient was diagnosed with sympathetic ophthalmia, and the right eye with bare light perception vision, was enucleated for pain control.

Case 5 A 45-year-old white woman developed bilateral uveitis 16 months following surgical repair of a rhegmatogenous retinal detachment of the right eye complicated by recurrent vitreous hemorrhages and no light perception vision (Chan, C-C. et al., Ophthalmology (1986) 93:690–5). A clinical diagnosis of sympathetic ophthalmia was made, and the right eye was enucleated for pain control.

Case 6 A 60-year-old white man developed bilateral uveitis 4 months after undergoing multiple surgical procedures for a retinal detachment that followed cataract extraction of the left eye (Chan, C-C. et al., Ophthalmology (1986) 93:690–5). The patient was diagnosed with sympathetic ophthalmia and neovascular glaucoma developed in the left eye. The left eye became blind and was enucleated for control of pain.

Materials and Methods for Demonstrating Cell Adhesion Molecules in Posterior Uveitis.

The six enucleated eyes for six patients with uveitis were immediately snap frozen in a dry ice and methylbutane bath and embedded in O.C.T. (Miles Laboratory, Naperville, Ill. Seven normal eye bank eyes were also snap frozen and used as controls. Six micron frozen sections of the posterior segment of all eyes were prepared and immunohistochemical staining was performed using an avidin-biotin-complex technique (Hsu, S. M. et al., J. Histochem. Cytochem. (1981) 29:557–580). The primary antibodies included monoclonal antibodies against ICAM-1 (CD45) (Courtesy of Dr. Toshi Nakayama, National Cancer Institute, Bethesda, Md.), LFA-1α (CD11a) and LFA-1β (CD18) (Becton Dickinson Immunocytometry Systems, San Jose, Calif.), ELAM-1 (Courtesy of Dr. Walter Newman, Otsuka America Pharmaceutical, Inc. Research Laboratories, Rockville, Md., and TNF-α and TNF-β (Genzyme, Boston, Mass.). Mouse ascites fluid containing 1 to 2 μg of protein per milliliter was the control primary antibody, and biotin conjugated, horse antimouse IgG was the secondary antibody. The avidin-biotin-peroxidase complex was applied, and 3,3'-diaminobenzidine-$Ni_2SO_4$-$H_2O_2$ was the substrate. The remaining ocular tissue was stained with hematoxylin and eosin for routine histopathologic examination.

Cell lines producing the above monoclonal antibodies are deposited with the American Type Culture Collection, (12301 Parklawn Drive, Rockville, Md. 20852, U.S.A.) and have been assigned ATCC Accession Numbers as follows: Anti-murine ICAM-1 (ATCC CRL 1878); Anti-human LFA-1β subunit (ATCC HB 203); Anti-human MAC-1 (ATCC HB 204); and Anti-LFA-1β unit and MAC-1β unit (ATCC TIB 218). The above antibodies are commercially available from the following sources: mouse anti-human ICAM-1 (CD54), Biosource International, Camarillo, Calif. catalog no. CT-CD54-UN; and mouse anti-ICAM-I (CD54), Accurate Chemical and Scientific Corp., Westbury, N.Y., catalog no. YSRT MCA 532; mouse anti-human LFA-1, Dako Corporation, Carpinteria, Cailf. catalog no. M782; antimouse LFA-1(CD11)/MAC-1, Sera-Lab, Ltd., Crowley Down, Sussex, England, catalog nos. MAS 504 cf/MAS 504 ce; rabbit anti-human TNF-α, Genzyme, Boston, Mass., catalog no. IP-300; and mouse anti-human ELAM-1, Biosource International, Camarillo, Calif. catalog no. BM-ELAM-2.

Immunohistochemical staining was interpreted by two, masked observers and compared to normal control eyes. Hematoxylin and eosin stained sections were also interpreted by two masked observers, and pathologic diagnoses were confirmed. Histopathologic findings were then correlated with the areas where immunohistochemical staining was noted.

Materials and Methods for Demonstrating Expression of Endothelial Leukocyte Adhesion Molecule-1 in Endotoxin Induced Uveitis.

EIU was induced in 59, female Lewis rats weighing 200 grams (Charles River, Wilmington, Mass. in three separate experiments by injecting 100 μg of *Salmonella typhimurium* endotoxin (LPS) (Difco, Detroit, Mich. into one footpad. All animals were treated in accordance with ARVO Resolution on Use of Animals in Research. Eyes were examined for clinical signs of inflammation under an operating microscope. Animals were then sacrificed and both eyes enucleated at 2 hour intervals from the time of injection until 48 hours post-injection. One eye was placed in 10% buffered formalin for routine histopathology. The other eye was embedded in OCT (Miles Laboratory, Naperville, Ill. and snap frozen.

Formalin fixed eyes were embedded in methylmethacrylate and 3 micron thick sections were stained with hematoxylin-eosin. Immunohistochemical staining was performed on 5 micron frozen sections using an avidin-biotin-peroxidase complex (ABC) method (Kim, M. K. et al., Curr. Eye Res. (1986) 5:869). The primary antibodies included OX6 (anti-RT1B antibody) (Sea-lab Westbury, N.Y.) and ELAM-1 (anti-human ELAM-1 that cross reacts with rat ELAM-1 courtesy of Dr. M. P. Bevilacqua). Mouse ascites fluid containing 1 to 2 μg of protein per milliliter was the control primary antibody, and biotin conjugated, goat antimouse IgG was the secondary antibody. Slides were graded by two, masked observers. The degree of immunohistochemical staining was compared with a normal eye and graded according to the scale previously described (Kim, M. K. et al., Curr. Eye Res. (1986) 5:869).

EXAMPLE 1

Expression of Cell Adhesion Molecules in Posterior Uveitis

Figures 1A, 1B:
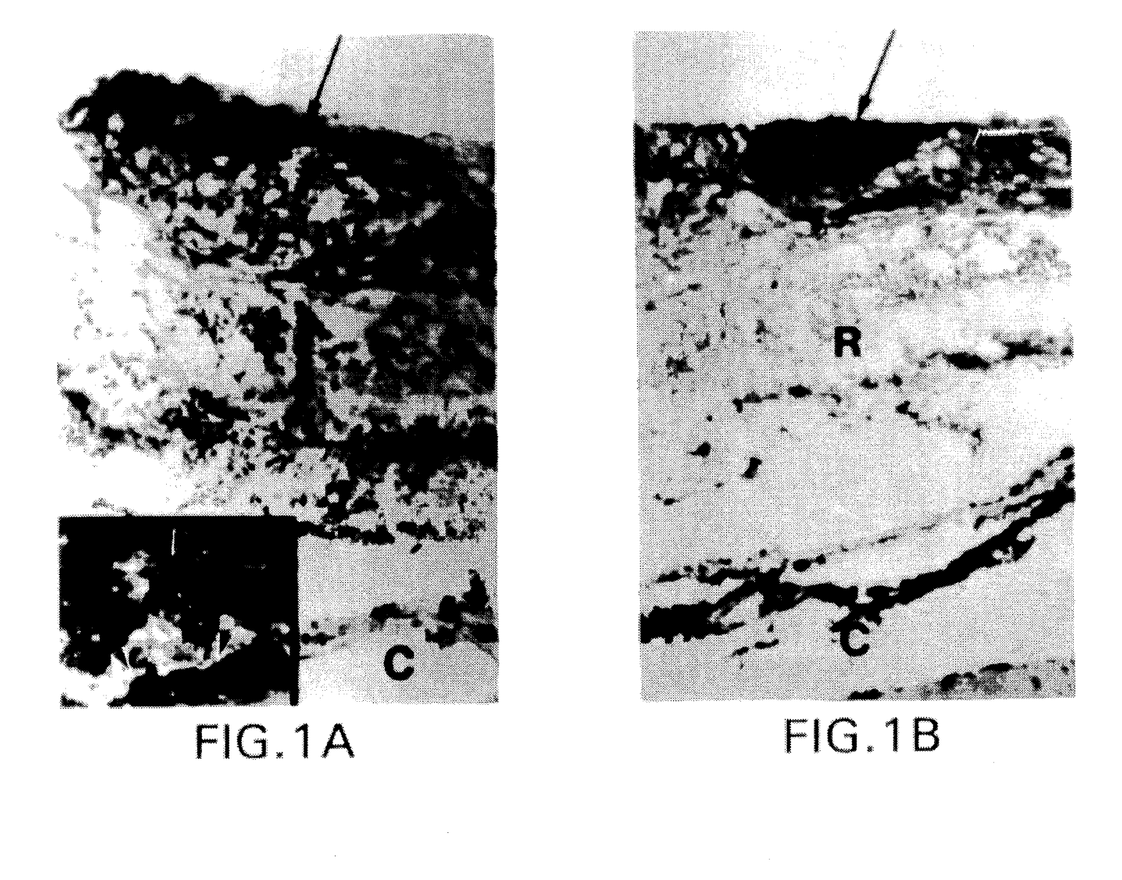
FIG. 1A Immunohistochemical staining for LFA-1. Infiltrating lymphocytes in an area of retinal vasculitis stain intensely for LFA-1α.
FIG. 1B. Immunohistochemical staining for LFA-1, showing the lymphocytes depicted in FIG. 1A also staining intensely for LFA-1β (original magnification× 200).
Figure 2A:
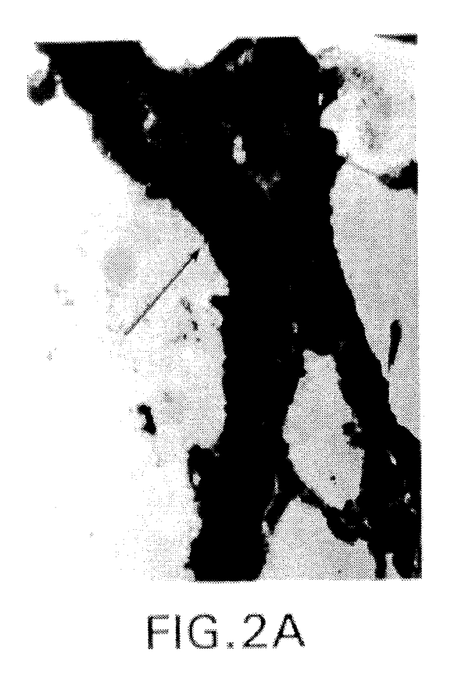
FIG. 2A. Immunohistochemical staining for ICAM-1. The retinal pigment epithelium stains positively for ICAM-1 (arrow).
Figure 2B:
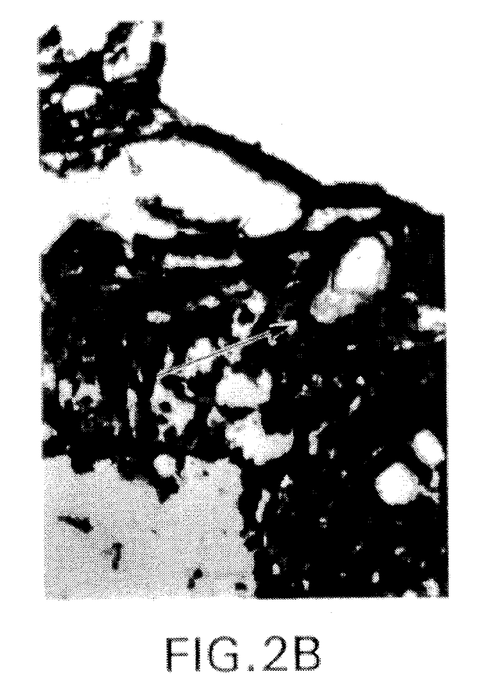
FIG. 2B. Immunohistochemical staining for ICAM-1. The retinal vascular endothelium in an area of inflammation stains strongly for ICAM-1 (arrow)(original magnification × 400).
Figure 3:
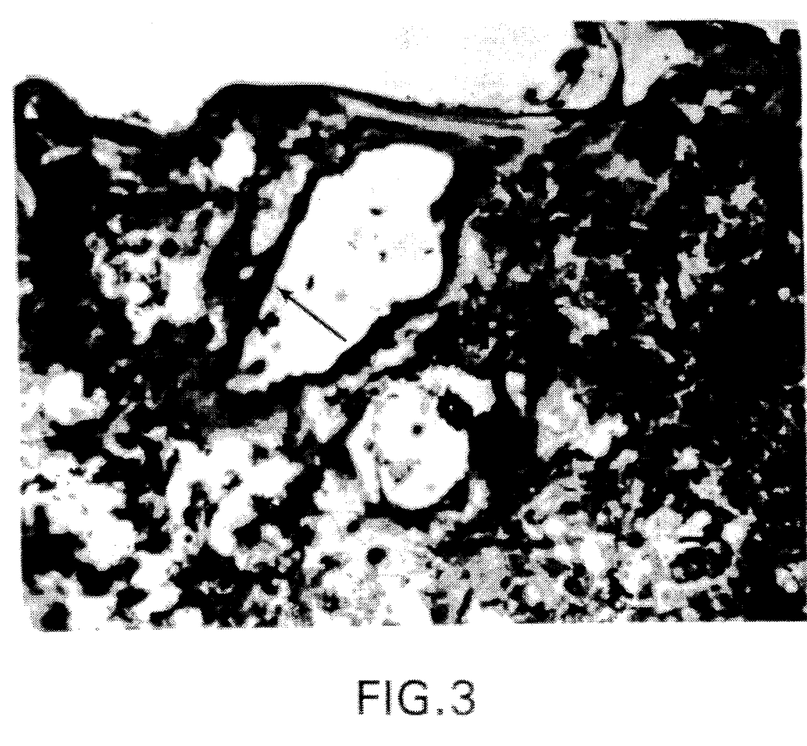
FIG. 3. Immunohistochemical staining shows that ELAM-1 is expressed on the retinal vascular endothelium (arrow) in a case of sympathetic ophthalmia (case 4) (original magnification×400).

Pathologic diagnoses matched the clinical diagnoses in all 6 cases. Three eyes (cases 4, 5 and 6) had histopathologic findings consistent with sympathetic ophthalmia, and the other three eyes were diagnosed as sarcoidosis (case 1), Vogt-Koyanagi-Harada syndrome (case 2), and subretinal fibrosis and uveitis syndrome (case 3). LFA-1 and ICAM-1 were expressed in all 6 eyes with uveitis, but in none of the normal control eyes (Table 1). Both LFA-1α and LFA-1β were expressed on almost all of the inflammatory cells, particularly lymphocytes, infiltrating the eyes with uveitis (FIGS. 1A and 1B). Cells appeared to stain more intensely with the anti-LFA-1β antibody. ICAM-1 was uniformly expressed on the RPE in cases 2–6 (FIG. 2A), and expressed on some of the RPE cells in case 1. ICAM-1 was also expressed on the endothelium of blood vessels in the retina and choroid in areas of inflammation (FIG. 2B) of all 6 eyes with uveitis, and on glial cells in the retina (cases 2, 3, and 6). ICAM-1 and LFA-1 were not expressed constitutively on any cells in the control eyes. ELAM-1 was only expressed on the vascular endothelium in one eye with active sympathetic ophthalmia (case 4) (FIG. 3), but not in any other uveitic eye or in any of the control eyes.

Figure 4:
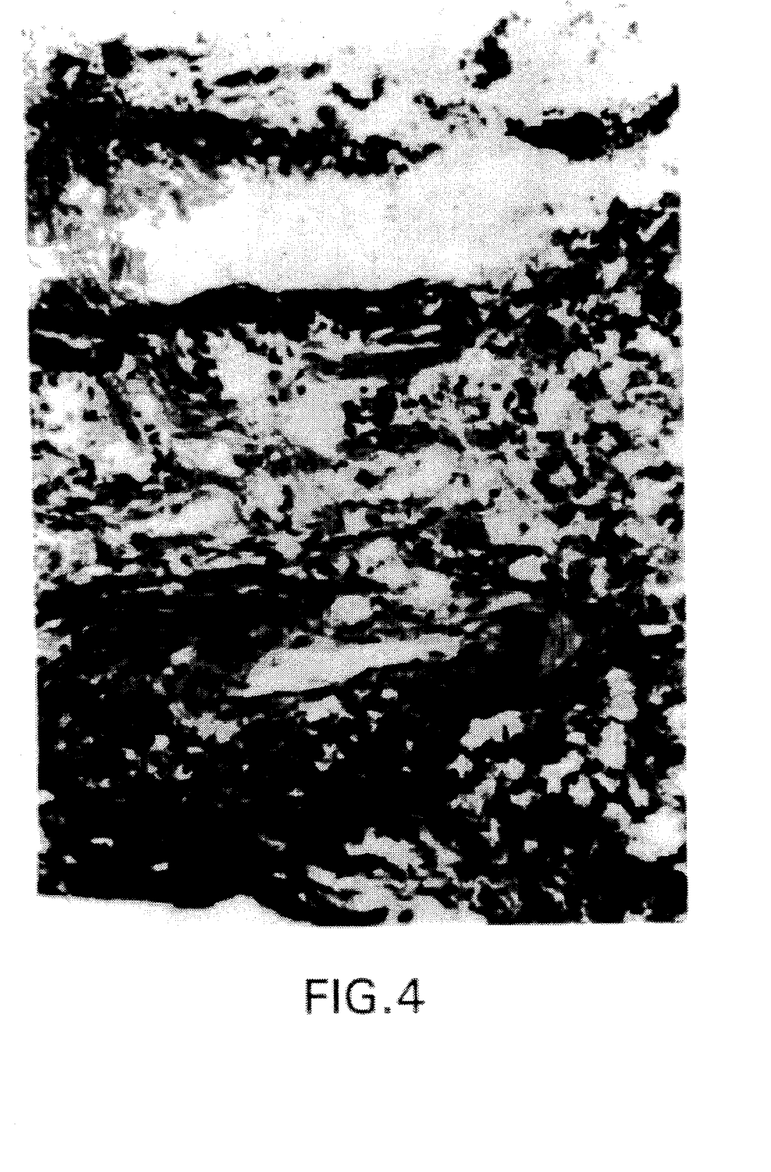
FIG. 4. Immunohistochemical staining for TNF-α. Inflammatory cells in the retina stain intensely for TNF-α (arrows) (original magnification×400).

The results of immunohistochemical staining for TNF-α and TNF-β are also listed in Table 1. All eyes with uveitis stained positively for TNF-α in the areas of inflammation (FIG. 4). Four of the six uveitic eyes showed mild staining for TNF-β (cases 1, 2, 3 and 6), and two uveitic eyes showed no staining with antibody against TNF-β. None of the control eyes stained positively for either TNF-α and TNF-β.

LFA-1 was strongly expressed on the majority of inflammatory cells in the six eyes with uveitis. LFA-1, also known as CD11a/CD18, is a member of the integrin family of cell adhesion molecules, and is expressed on leukocytes including T lymphocytes (Springer, T. A., Nature (1990) 346:425–434; Dustin, M. L. et al., J. Immunol. (1986) 137:245–254; Rothlein, R. et al., J. Immunol. (1986) 137:1270–1274). Each integrin molecule is composed of an alpha and beta subunit. The CD11a antibody is directed against the alpha subunit of LFA-1 and the CD18 antibody against the beta subunit. The ligation of the T cell receptor causes the activation of LFA-1 in lymphocytes in an antigen specific manner (Turner, J. M. et al., Cell (1990) 60:75514 765). This may be an important mechanism that allows blood cells to circulate unimpeded until they are activated at sites of inflammation, after the expression of cell adhesion molecules allows the cells to locate and make contact with the appropriate counter-receptor.

The counter-receptor of LFA-1 is ICAM-1. In contrast to LFA-1 which is only expressed on leukocytes, ICAM-1 is found on a multitude of cells (Kishimoto, T. K. et al., Adv. Immuno. (1989) 46:149–182). In the eye, ICAM-1 may be weakly expressed constitutively on the corneal endothelium and cultured RPE (Elner, V. M. et al., Am. J. Path. (1991) 138:525–536; Forrester, J. V. et al., Curr. Eye Res. (1990) 9 (Supp):183–191). ICAM-1 was found to be strongly expressed on the RPE, retinal and choroidal vascular endothelium, and on glial cells (Müller cells) in the retina in eyes with clinical and histopathologic evidence of active uveitis.

Expression of ICAM-1 and LFA-1 is felt to be important for the binding of leukocytes to target cells. Inflammatory cells in the 6 eyes with active uveitis expressing LFA-1 were located adjacent to resident cells expressing ICAM-1. ICAM-1 was moderately to markedly expressed on the vascular endothelium and RPE of all 6 eyes with uveitis, and lymphocytes were only found adjacent to ICAM-1 expressing cells. In cases 2–6, ICAM-1 was markedly and uniformly expressed on the RPE, and the adjacent choroid was infiltrated with LFA-1 expressing lymphocytes. In contrast, ICAM-1 was not uniformly expressed on the RPE in case 1, and a few lymphocytes were observed in the adjacent choroid. These findings suggest that ICAM-1 expression may be integral to the migration of inflammatory cells into the choroid and retina and important for subsequent cell-cell interactions which lead to tissue damage. Forrester and colleagues have demonstrated that antibodies to ICAM-1 and LFA-1 will almost totally inhibit lymphocyte-RPE interactions, and suggest that the binding of LFA-1 to ICAM-1 is a major adhesion mechanism involved in the initial access of autoreactive or activated lymphocytes to the retina at the blood-RPE interface (Liversidge, J. et al., Immunology (1990) 71:390–396). Elner and associates have similarly demonstrated that ICAM1 mediated binding of neutrophils to the corneal endothelium is blocked by antibody to ICAM-1 (Elner et al (1991) Am. J. Path. 138:525–536). Leukocyte binding is not completely blocked by antibodies to ICAM-1 or LFA-1 suggesting that other cell-cell interactions are important in cell adhesion. For example, ICAM-2 is also a ligand for LFA-1, and important for cell binding (Springer, T. A., Nature (1990) 346:425–434).

An important issue concerns the regulation of adhesion molecule expression. The secretions of cytokines, particularly by the infiltrating T lymphocytes, probably plays an important regulatory function. Gamma-interferon, interleukin-1, and tumor necrosis factor cause the strong induction of ICAM-1, although different cells vary as to which cytokines will induce ICAM1 expression (Kaminska, G. M. et al., Invest. Ophthalmol. Vis. Sci. (1991) 32 (Supp):677; Springer, T. A., Nature (1990) 346:42514 434; Kishimoto, T. K. et al., Adv. Immuno. (1989) 46:149–182; Liversidge, J. et al., Immunology (1990) 71:390–396; Springer, T. A. et al., A. Rev. Immun. (1987) 5:223–252; Dustin, M. L. et al., J. Cell Biol. (1988) 107:321–331; Norris, D. A., J. Invest. Dermatol. (1990) 95:111S–120S). The presence of gamma-interferon in eyes with active uveitis, and a predominant T cell infiltration in the retina and choroid in eye with sympathetic ophthalmia and idiopathic uveitis were previously reported (Hooks, J. J. et al., Invest. Ophthalmol. Vis. Sci. (1988) 29:1444–1451). Wakefield and colleagues have also demonstrated increased levels of gamma interferon in the iris biopsies from patients with uveitis (Wakefield, D. et al., Invest. Ophthalmol. Vis. Sci. (1991) 32 (Supp):1186). Like gamma-interferon, TNF-α can induce expression molecules and lead to the binding of leukocytes. TNF-β (lymphotoxin) is a related cytokine that is produced by T and B lymphocytes, but may be less active in inducing adhesion molecule expression (Broudy, V. C. et al., J. Immunol. (1987) 138:4298–4302; Locksley, R. M. et al., J. Immunol. (1987) 139:1891–1895).

TNF-α was present in the areas of inflammation in all the uveitic eyes and may have increased ICAM-1 expression on the adjacent vascular endothelium. In contrast, 4 of 6 uveitic eyes stained weakly for the less active TNF-β.

Although ICAM-1 was expressed in all eyes with ocular inflammation, ELAM-1 was only weakly expressed on choroid blood vessels in one eye with early, active sympathetic ophthalmia. Histopathology of this case showed neutrophils invading the choroid. ELAM-1 is a cell surface-glycoprotein, expressed by cytokine-activated endothelium, that predominantly binds neutrophils (Bevilacqua, M. P., Science (1989) 243:1160–64). ELAM-1 expression on the corneal endothelium 10 hours after the injection of endotoxin into the footpad of Lewis rats with subsequent binding of neutrophils was demonstrated. Expression of ELAM1 developed 2 hours after the local injection of endotoxin into the skin of baboons, and was absent by 9 hours after injection (Munro, J. M. et al., Lab. Invest. (1991) 64:295–299). This early and transient expression of ELAM-1 may explain why ELAM-1 expression was not present in these eyes with prolonged inflammation.

The six eyes studied had histopathologic evidence of lymphocytic infiltration predominantly involving the retina and choroid. Sympathetic ophthalmia, VKH, sarcoidosis, and the subretinal fibrosis syndrome are all presumed autoimmune diseases of the eye. The etiology of ocular inflammation in these disorders remains unknown, although an immune reaction against retinal antigens such as retinal S-antigen and interphotoreceptor binding protein may be causative in some cases. The mechanism by which inflammatory cells migrate into the eye in uveitis is also not well documented. The demonstration of expression of ICAM-1 on the RPE, glial cells, and vascular endothelium and the presence of lymphocytes strongly expressing LFA-1 adjacent to these ICAM-1 expressing cells suggests that the ICAM-1/LFA-1 interaction is important in the development of ocular inflammation in these cases. Antibodies against ICAM-1 and LFA-1 can significantly inhibit the binding of leukocytes, and monoclonal antibodies against these adhesion molecules have decreased inflammatory damage in animal models of acute respiratory distress syndrome and meningitis (Ismail, G. et al., Blood (1987) 69:1167–1174; Tuomanen, El. et al., J. Exp. Med. (1989) 170:959–968). Monoclonal antibodies against ICAM-1 and LFA-1 can also provide effective anti-inflammatory therapy for some cases of uveitis.

TABLE 1

Expression of cell adhesion molecules and TNF in eyes with uveitis

| Case | Diagnosis | LFA-1α | LFA-1β | ICAM-1 | ELAM-1 | TNF-α | TNFβ |
|---|---|---|---|---|---|---|---|
| 1 | Sarcoidosis | ++<br>L | +++<br>L | + to ++<br>VE | – | ++<br>SI | +<br>SI |
| 2 | VKH | +<br>L | +<br>L | ++<br>VE,RPE,GL | – | +++<br>SI | +<br>SI |
| 3 | SRFUS | +<br>L | ++<br>L | ++<br>VE,RPE,GL | – | +<br>SI | +<br>SI |
| 4 | SO | ++<br>L | +++<br>L | ++<br>VE,RPE | +<br>VE | +++<br>SI | –<br>SI |
| 5 | SO | ++<br>L | ++<br>L | +++<br>VE,RPE | – | +++<br>SI | –<br>SI |
| 6 | SO | ++<br>L | +++<br>L | +++<br>VE,RPE,GL | – | +++<br>SI | +<br>SI |

VKH = Vogt-Koyanagi-Harada syndrome,
SRFUS = Subretinal fibrosis and uveitis syndrome,
SO = sympathetic opthalmia
GL = glial cells,
SI = site of inflammation,
L = lymphocyte,
RPE = retinal pigment epthelium,
VE = vascular endothelium.
Intensity of staining:
(–) = none,
(+) = mild,
(++) = moderate,
(+++) = marked.

EXAMPLE 2

Expression of Endothelial Leukocyte Adhesion Molecule-1 in Endotoxin Induced Uveitis Clinical and histopathologic evidence of inflammation occurred 16 hours post-injection. Clinical signs of inflammation included iris hyperemia and a fibrinous exudate in the anterior chamber. On pathologic examination, neutrophils and monocytes were seen in the iris and ciliary body. Proteinaceous material, fibrin debris, and neutrophils were evident in the anterior chamber, with many neutrophils adherent to the corneal endothelium.

The time course for the expression of MHC class II antigen and ELAM-1 in the anterior segment of the eye following the induction of EIU are shown in Table 2. At the time of endotoxin injection MHC class II antigen was weakly expressed on one or two resident cells in the stroma of the ciliary body and iris. Four hours after injection of LPS MHC class II antigen was expressed on epithelial and stromal cells of the iris and the ciliary body. Eight hours post-injection, MHC class II antigen was expressed on the corneal endothelium, and MHC class II antigen persisted on ocular tissue 48 hours after injection.

Figure 5:
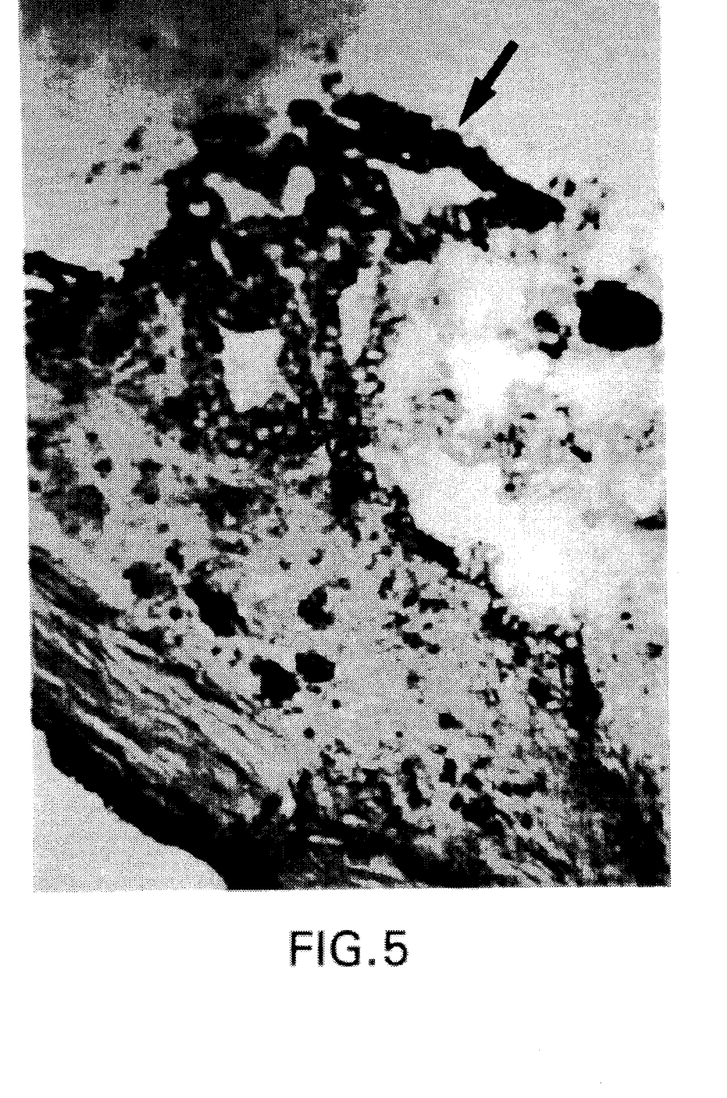
FIG. 5. Light micrograph of the ciliary body 10 hours after the injection of *Salmonella typhimurium* endotoxin. Immunostaining shows strong expression of ELAM-1 on the vascular endothelium (arrow) and on scattered resident cells (magnification× 400).
Figure 6A:
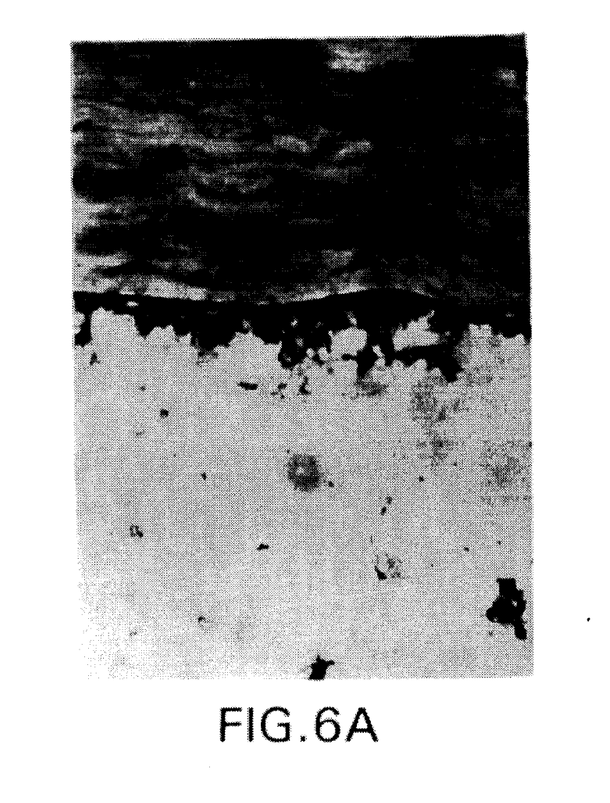
FIG. 6. Light micrograph of the cornea from two rats 22 hours after injection of *Salmonella typhimurium* endotoxin. Immunostaining shows strong expression of ELAM-1 on the corneal endothelium. Inflammatory cells are adherent to the corneal endothelium where ELAM-1 is expressed (magnification× 400).
Figure 6B:
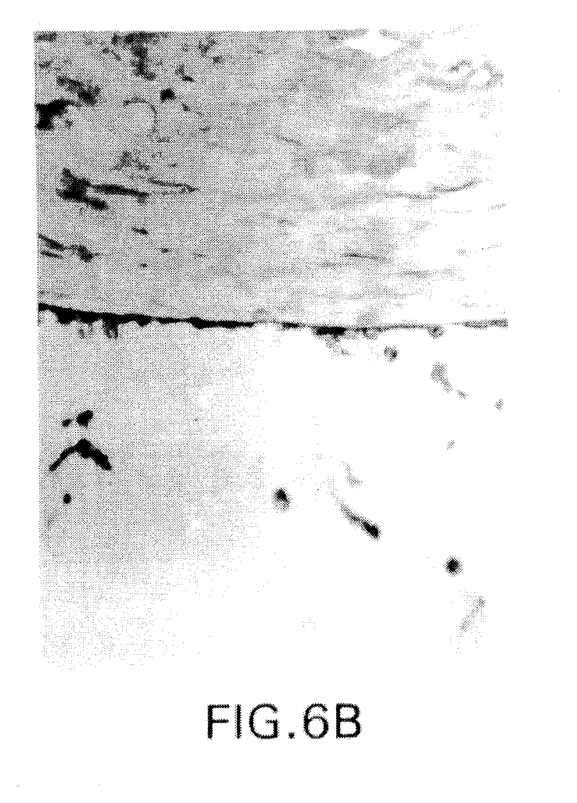

ELAM-1 did not appear to be expressed constitutively on any ocular tissue, but was first expressed on stromal and vascular endothelial in the iris and ciliary body 10 hours after the injection of LPS (FIG. 5). ELAM-1 was later expressed on the corneal endothelium 22 hours post-injection (FIG. 6). At this time, neutrophils were present in the anterior chamber, many adherent to the corneal endothelium where ELAM-1 was expressed. Between 24 and 48 hours after injection, expression of ELAM-1 on the corneal endothelium and cells in the ciliary body and iris gradually diminished.

These results suggest that ELAM-1 is an inducible cell adhesion molecule, which was expressed on vascular endothelial cells in the iris and ciliary body at the onset of EIU, and expressed on the corneal endothelium at the peak of inflammation. ELAM-1 is cell surface glycoprotein, expressed by cytokine-activated endothelium, that predominantly binds neutrophils (Bevilacqua, M. P. et al., Science (1989) 243:1160). More recently, Picker et al. showed that skin-homing memory T lymphocytes bound to ELAM-1 transfected COS cells (Picker, L. J. et al., Nature (1991) 349:796), and Shimizu et al. showed that ELAM-1 contributes to the greater adhesion to endothelium of memory T cells than naive T cells (Shimizu, Y. et al., Nature (1991) 349:799). Munro et al. studied the role of ELAM-1 on the recruitment of neutrophils in the local endotoxin response in the skin of baboons (Munro, J. M. et al., Lab. Invest. (1991) 295:295). Endothelium in control skin did not express ELAM-1 but developed 2 hours after injection of endotoxin with concurrent extensive adhesion and extravasation of neutrophils. ELAM-1 expression subsequently decreased was absent by 9 hours.

ELAM-1 was first expressed in the eye 8 hours after injection of endotoxin and gradually diminished between 24 and 48 hours after injection. However, endotoxin was injected into the footpad of rats, therefore, the resultant ocular inflammation was not a local endotoxin response. This probably explains the delay in ELAM-1 expression in the eye. ELAM-1 expression on the vascular endothelium of the ciliary body and iris occurred before neutrophils could be identified histopathologically, suggesting a role in neutrophil recruitment, and neutrophils adhered to the corneal endothelium following ELAM-1 expression. Corneal and vascular endothelium are derived from different embryonic tissues. Corneal endothelium develops from cranial neural crest cells, and the endothelium of ocular blood vessels derives from mesoderm. Nevertheless, Elner and colleagues demonstrated the expression of intercellular adhesion molecule-1 (ICAM-1) on the corneal endothelium and corneal stroma keratocytes, and showed that antibody to ICAM-1 effectively blocked neutrophil binding to corneal endothelium of cell cultures and whole corneas (Elner, V. M., Am. J. Path. (1991) 138:525–536).

The accumulation of neutrophils in the anterior chamber of the eye and the adherence of leukocytes to the corneal endothelium are important clinical signs of ocular inflammation. Previous studies showed that ICAM-1 is important in neutrophil binding to the corneal endothelium. This is the first study to demonstrate the expression of ELAM-1 on ocular tissue. ELAM-1 was not expressed constitutively, but appeared on vascular endothelium of the iris and ciliary body and on the corneal endothelium after the induction of EIU.

TABLE 2

Kinetics of MHC class II antigen and ELAM-1 expression in EIU

| TIME AFTER INJECTION OF ENDOTOXIN | FINDINGS |
| --- | --- |
| 4 HOURS | Class II antigen expressed on cells in the iris and ciliary body |
| 8 HOURS | Class II antigen expressed on the corneal endothelium |
| 10 HOURS | ELAM-1 expressed on the vascular endothelium and on resident cells in the iris and ciliary body |
| 16 HOURS | Clinical and histopathologic evidence of disease |
| 22 HOURS | ELAM-1 expressed on the corneal endothelium |

EXAMPLE 3

Use of Monoclonal Antibody Against MAC-1 to Prevent Inflammation in Endotoxin Induced Uveitis Local or systemic injection of the lipopolysaccharide (LPS) constituents of the cell wall of gram-negative bacterial will produce inflammation in several organs including the eye (Rosenbaum, J. T. et al. (1980) Nature 286:611; Bhattacherjee, P. et al. (1983) Invest Ophthalmol Vis Sci 24:196; Cousins, S. W. et al. (1984) Exp Eye Res 39:665). Injection of LPS into the footpad of certain animals, including species of rats, mice, and rabbits, produces an anterior uveitis characterized by iris hyperemia, and increased protein an inflammatory cell accumulation in the anterior uvea and anterior chamber. This inflammatory process is termed endotoxin-induced uveitis (EIU), and is used as an animal model for ocular inflammation. EIU is associated with an increase in systemic vascular permeability (Cousins, S. W. et al. (1984) Exp Eye Res 39:665; Cousins, S. W. et al. (1982) Infect Immun 36:730; Howes et al. (1970) Arch Ophthal 84:360), alterations in antibody and interferon production (Steeg et al. (1982) J Immunol 129:2402; Uchiyama et al. (1978) J Immunol 121:2340; Maehara, N. et al. (1977) Infect Immun 15:78), and increased levels of prostaglandins and C5a in the eye (Rosenbaum, J. T. et al. (1984) Invest Ophthalmol Vis Sci 25:1184). Cell adhesion molecules are expressed on ocular structures during EIR. HLA class II antigen is expressed on the cornea, iris, ciliary body, and retinal pigment epithelium, and ELAM is expressed on cells of the iris, ciliary body, and corneal endothelium during EIU (Kim, M. K. et al. (1986) Curr Eye Res 5:869).

Mac-1 (CD11b/CD18) is a cell adhesion molecule important for neutrophil and monocyte migration to areases of inflammation. The effect of treatment with a monoclonal antibody against Mac-1 (Courtesy of Dr. Hugh Rosen) on the development of endotoxin induced uveitis (EIU) in C3H-HeN mice was studied. In two separate experiments, EIU was induced in a total of 48 mice by injecting 200 micrograms of Salmonella typhimurium endotoxin into one hind footpad. At the time of endotoxin injection, 24 mice received an intraperitoneal injection of 500 micrograms of anti-mac-1 antibody and 24 control mice received an intraperitoneal injection of 500 micrograms of rat IgG. Mice were sacrificed 24 hours after endotoxin injection, and both eyes were enucleated. The right eye was processed for routine histopathology, and the left eye was snap frozen for immunohistochemistry. Histopathologic sections of the eyes were graded by two, masked observers on a scale of 0 (no inflammation) to 4+(severe inflammation). The mean grade of ocular inflammation ± standard error was 0.54+0.08 for mice treated with antibody against Mac-1 and 2.48 ±0.16 for the control mice, (p<0.001). These data show that antibody against Mac-1 inhibits the development of endotoxin induced uveitis in mice, and suggests that anti-Mac-1 antibody may be useful for treating acute ocular inflammation.

Thus antibodies against cell adhesion molecules can be used in treating ocular inflammation. In this example, antibody against MAC-1 to prevent inflammation was used, however, similar results can be obtained using substances to block a wide array of these molecules. In this example, the antibodies were administered systemically, but the treatment can be administered by a periocular injection or topically in the form of eye drops or ophthalmic ointment.

EXAMPLE 4

Treatment of Experimental Autoimmune Uveitis

18 B10.A mice were immunized with 50 micrograms of IRBP and 0.25 mg of complete Freund's adjuvant by injecting each thigh with 0.1 ml of the above emulsion. Animals also received an intraperitoneal injection of 0.5 micrograms of pertussis toxin in 0.1 ml of saline. Animals were then divided into three groups receiving daily intraperitoneal injections containing 0.25 mg of anti-ICAM-1 antibody, anti-LFA-1 antibody, and rat IgG, respectively. The fundi of these mice were examined under a dissecting microscope 14 and 21 days following injection of IRBP. All animals were sacrificed 21 days after injection of IRBP. One eye was placed in 4% glutaraldehyde for 20 minutes and then transferred into 10% buffered formalin for routine histopathology. The other eye was immediately snap frozen in OCT.

Figure 7A:
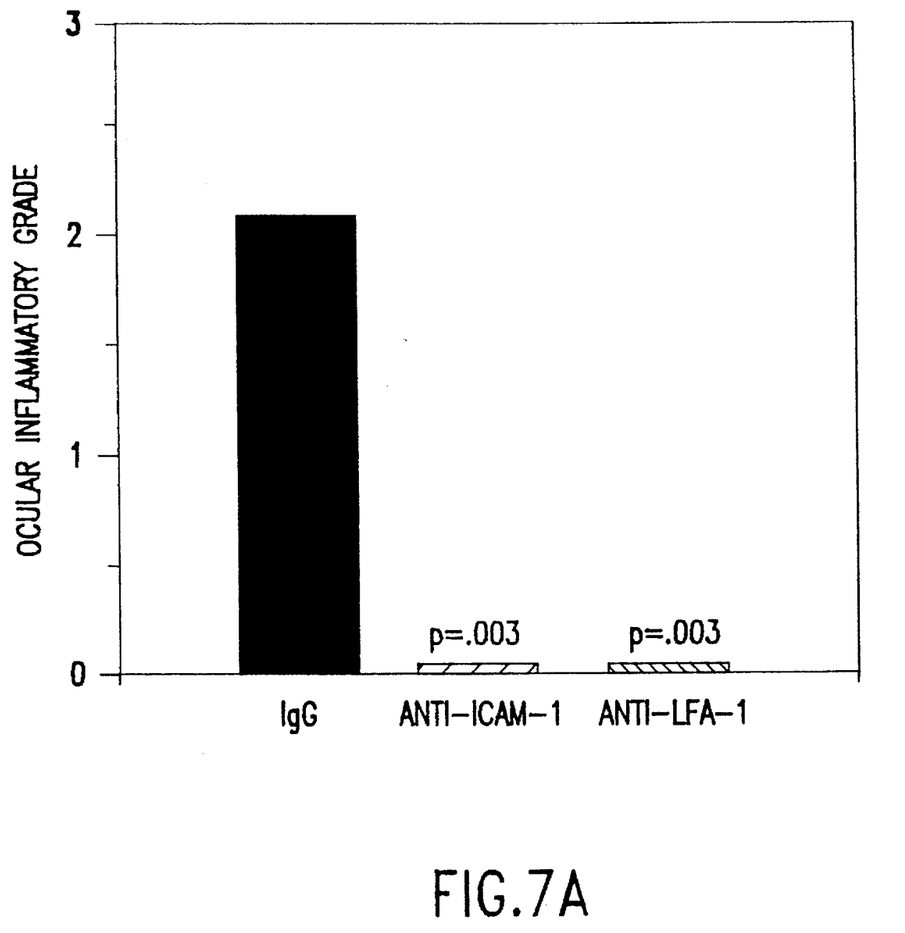
FIG. 7A. Fundoscopy day 14 with anti-ICAM-1 and anti-LFA-1 treatment and IgG control treatment.
Figure 7B:
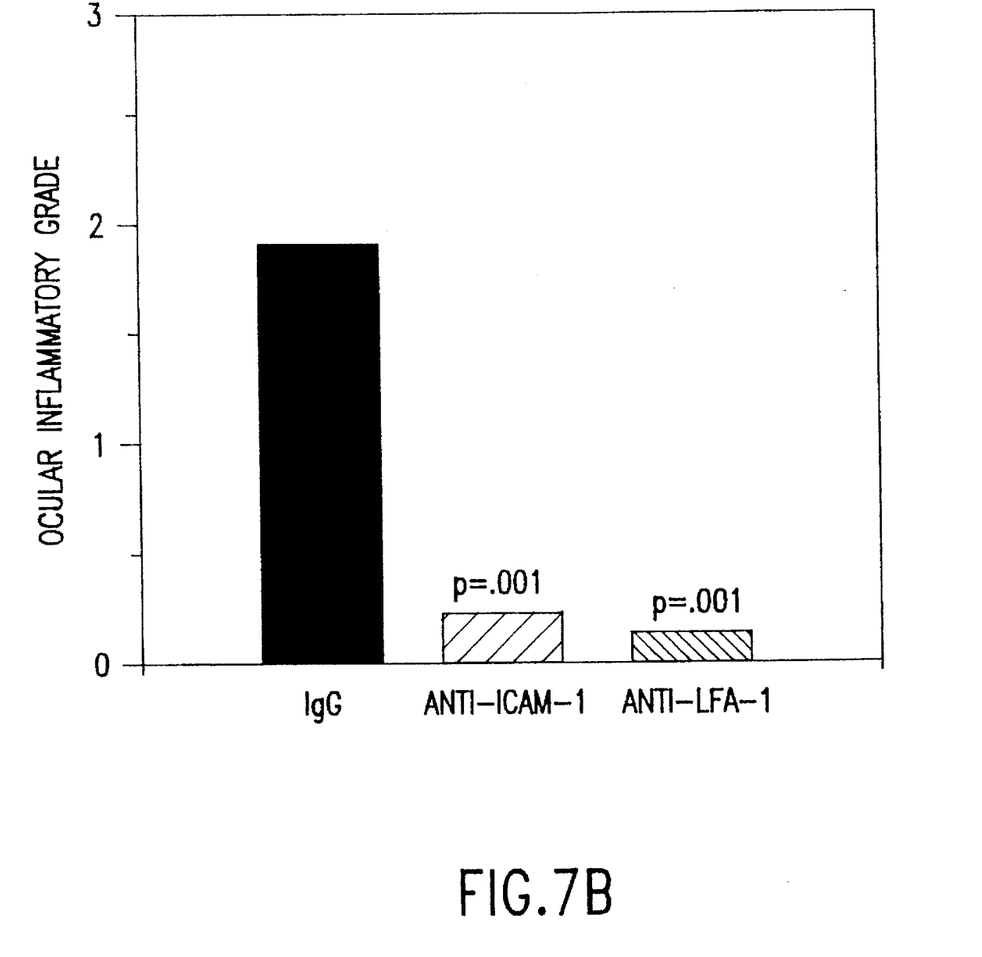
FIG. 7B. Fundoscopy day 21 with anti-ICAM-1 and anti-LFA-1 treatment and IgG control treatment.
Figure 7C:
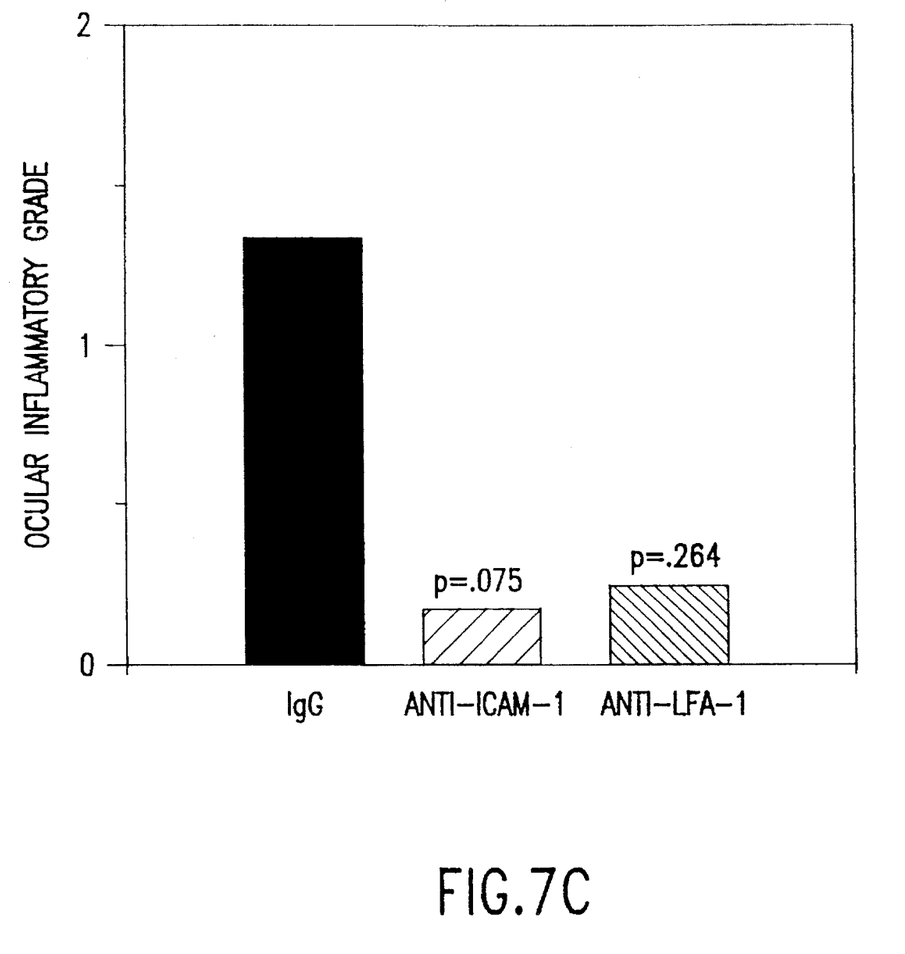
FIG. 7C. Histology day 21 with anti-ICAM-1 and anti-LFA-1 treatment and IgG control treatment.
Figure 8:
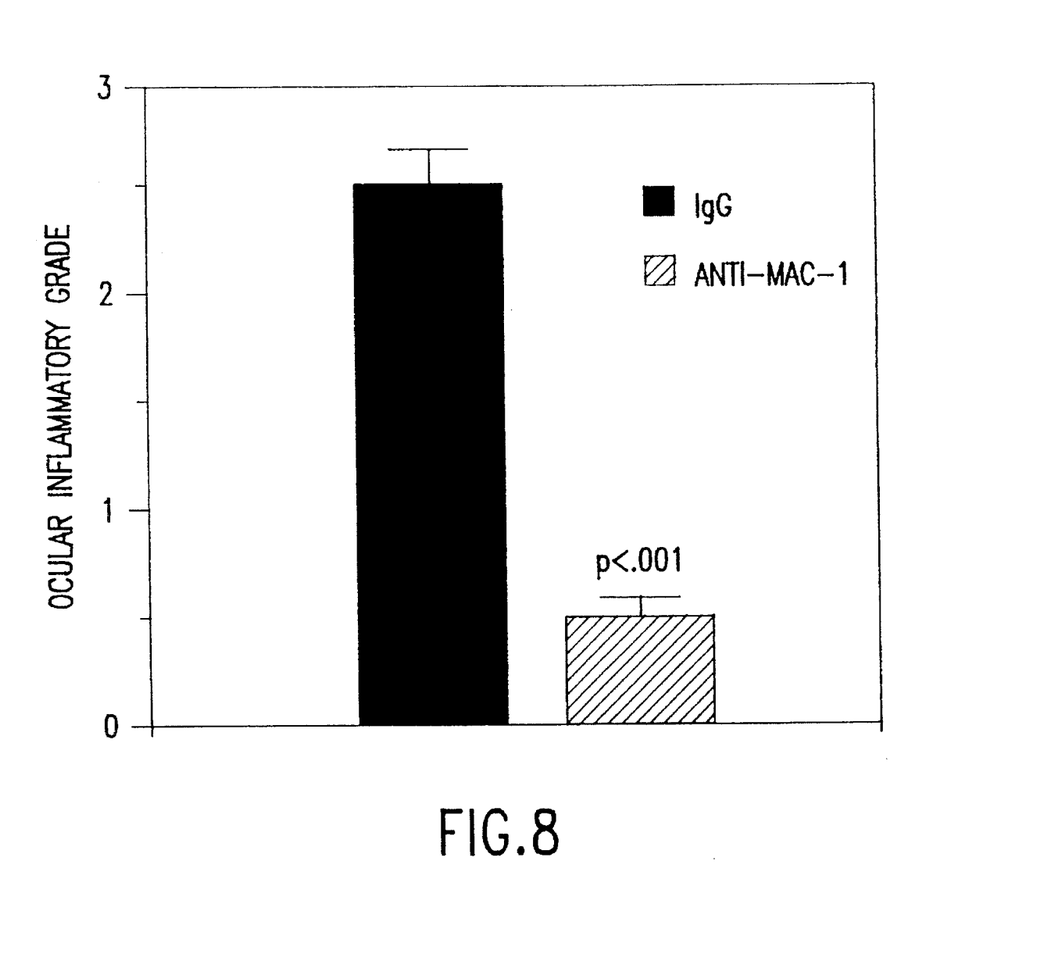
FIG. 8. Anti-Mac-1 vs IgG.

One mouse in the control group treated with rat IgG died on day two of the experiment. The clinical grade of ocular inflammation by fundus examination on day 14 was 0 for the mice treated with anti-ICAM-1 antibody, 0 for the mice treated with anti-LFA-1 antibody, and 2.05 for the control mice treated with rat IgG (P=0,003) (FIG. 7A). The clinical grade of ocular inflammation by fundus examination on day 21 was 0.23 for the mice treated with anti-ICAM-1 antibody, 0.17 for the mice treated with anti-LFA-1 antibody, and 1.95 for the control mice treated with rat IgG (P=0,001) (FIG. 7B). All mice were sacrificed 21 days after injection and the grade of ocular inflammation by histopathology was 0.17 for the mice treated with anti-ICAM-1 antibody, 0.23 for the mice treated with anti-LFA-1 antibody, and 1.3 for the control mice treated with rat IgG (P=0.75 and P=0.264, FIG. 7C and D, respectively). Although the differences and histologic grades of inflammation were not statistically significant, there was a definite trend toward statistical significance which can be expected when greater numbers of animals are tested.

Mice treated with daily intraperitoneal injections of monoclonal antibodies against ICAM1 and LFA-1 developed less clinical evidence of ocular inflammation based on funduscopic examination 14 and 21 days after immunization with IRBP when compared to control animals treated with intraperitoneal rat IgG. The funduscopic evidence of ocular inflammation was not only less severe, but developed later in the treated mice. Histopathology also showed that mice treated with antibodies to block ICAM-1 and LFA-1 developed less ocular inflammation than control animals. This study indicates that animals treated with monoclonal antibodies against ICAM-1 and LFA-1 develop ocular inflammation following the induction of experimental autoimmune uveitis.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method of treating an animal with acute ocular inflammation comprising administering to said animal an amount of an antibody having binding affinity for a cell adhesion molecule selected from the group consisting of ELAM-1, Mac-1, ICAM-1 and LFA-1 effective to bind the cell adhesion molecule such that said antibody binds the cell adhesion molecule and said treatment is effected.

2. The method of claim 1, wherein said inflammation results from trauma or disease.

3. The method of claim 1, wherein said inflammation is post-surgical inflammation.

4. The method of claim 1, wherein said inflammation results from post-surgical corneal graft rejection.

5. The method of claim 1, wherein said inflammation is posterior uveitis.

6. A method of blocking the interaction between a cell adhesion molecule and its respective ligand in an animal with acute ocular inflammation comprising administering to said animal an amount of an antibody having binding affinity for said cell adhesion molecule selected from the group consisting of ELAM-1, Mac-1, ICAM-1 and LFA-1 sufficient to block the interaction between the cell adhesion molecule and its respective ligand such that blocking of said molecule is effected.

7. The method of claim 6, wherein said inflammation results from trauma or disease.

8. The method of claim 6, wherein said inflammation is post-surgical inflammation.

9. The method of claim 6, wherein said inflammation results from post-surgical corneal graft rejection.

10. The method of claim 6, wherein said inflammation is posterior uveitis.

11. A method of treating ocular inflammation in an animal comprising administering to said animal an amount of an antibody having binding affinity for a cell adhesion molecule selected from the group consisting of LFA-1 and ICAM-1 effective to bind the cell adhesion molecule such that said antibody binds the cell adhesion molecule and said treatment is effected.

12. A method of treating ocular inflammation in an animal comprising topically administering to the eye of said animal an amount of an antibody having binding affinity for a cell adhesion molecule selected from the group consisting of ELAM-1, Mac-1, ICAM-1 and LFA-1, effective to bind the cell adhesion molecule such that said antibody binds the cell adhesion molecule and said treatment is effected.

* * * * *